United States Patent
Kikuchi et al.

(10) Patent No.: US 10,582,840 B2
(45) Date of Patent: Mar. 10, 2020

(54) ENDOSCOPE APPARATUS

(71) Applicant: OLYMPUS CORPORATION, Tokyo (JP)

(72) Inventors: Satoru Kikuchi, Tokyo (JP); Kazuo Banju, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 282 days.

(21) Appl. No.: 15/681,911

(22) Filed: Aug. 21, 2017

(65) Prior Publication Data

US 2017/0367566 A1  Dec. 28, 2017

Related U.S. Application Data

(63) Continuation of application No. PCT/JP2016/062567, filed on Apr. 20, 2016.

(30) Foreign Application Priority Data

May 14, 2015  (JP) ................. 2015-098872

(51) Int. Cl.
*A61B 1/00* (2006.01)
*A61B 1/05* (2006.01)
(Continued)

(52) U.S. Cl.
CPC .......... *A61B 1/053* (2013.01); *A61B 1/00009* (2013.01); *A61B 1/0051* (2013.01);
(Continued)

(58) Field of Classification Search
CPC ................ A61B 1/053; A61B 1/00009; G02B 23/2407; G06T 2207/20092; G06T 7/0002

See application file for complete search history.

(56) References Cited

U.S. PATENT DOCUMENTS

2009/0192524 A1  7/2009  Itkowitz et al.
2014/0194896 A1  7/2014  Frimer et al.
(Continued)

FOREIGN PATENT DOCUMENTS

EP   3 246 135 A1   11/2017
EP   3 385 039 A1   10/2018
(Continued)

OTHER PUBLICATIONS

Extended Supplementary European Search Report dated Jan. 2, 2019 in European Patent Application No. 16 79 2506.4.
(Continued)

*Primary Examiner* — Timothy J Neal

(74) *Attorney, Agent, or Firm* — Scully, Scott, Murphy & Presser, P.C.

(57) ABSTRACT

Provided is an endoscope apparatus provided with: an elongated insertion portion that is inserted into a body; an image-acquisition portion that has an imaging optical system disposed at a distal end of the insertion portion and that acquires two images having parallax for the same imaging subject; an identifying portion that identifies an image of an object, which is in close proximity to the imaging optical system, that is captured only in one of the two images acquired by the image-acquisition portion; and a close-proximity-image-removal processing portion that processes the image so that the image of the object identified by the identifying portion is removed from the image.

2 Claims, 9 Drawing Sheets

(51) Int. Cl.
*G02B 23/24* (2006.01)
*G06T 5/00* (2006.01)
*H04N 13/122* (2018.01)
*H04N 13/239* (2018.01)
*A61B 1/005* (2006.01)
*G06T 7/00* (2017.01)

(52) U.S. Cl.
CPC ...... *A61B 1/00183* (2013.01); *A61B 1/00193* (2013.01); *A61B 1/05* (2013.01); *G02B 23/2407* (2013.01); *G02B 23/2415* (2013.01); *G06T 5/005* (2013.01); *H04N 13/122* (2018.05); *H04N 13/239* (2018.05); *G06T 7/0002* (2013.01); *G06T 2207/10012* (2013.01); *G06T 2207/10068* (2013.01); *G06T 2207/20092* (2013.01); *H04N 2213/002* (2013.01)

(56) References Cited

U.S. PATENT DOCUMENTS

| | | |
|---|---|---|
| 2014/0276952 A1 | 9/2014 | Hourtash et al. |
| 2014/0371527 A1 | 12/2014 | Sato |
| 2016/0007826 A1 | 1/2016 | Frimer et al. |
| 2016/0007827 A1 | 1/2016 | Frimer et al. |
| 2016/0007828 A1 | 1/2016 | Frimer et al. |
| 2016/0051336 A1 | 2/2016 | Frimer et al. |
| 2016/0174955 A1 | 6/2016 | Frimer et al. |
| 2016/0270864 A1 | 9/2016 | Frimer et al. |
| 2017/0027654 A1 | 2/2017 | Frimer et al. |
| 2017/0035518 A1 | 2/2017 | Hourtash et al. |
| 2017/0282372 A1 | 10/2017 | Itkowitz et al. |
| 2018/0153630 A1 | 6/2018 | Hourtash et al. |

FOREIGN PATENT DOCUMENTS

| | | |
|---|---|---|
| JP | H05-285091 A | 11/1993 |
| JP | H05-316541 A | 11/1993 |
| JP | H10-309258 A | 11/1998 |
| JP | 2004-081277 A | 3/2004 |
| JP | 2007-029232 A | 2/2007 |
| JP | 2007-151862 A | 6/2007 |
| JP | 2012-220888 A | 11/2012 |
| JP | 2014-097431 A | 5/2014 |
| JP | 2014-146970 A | 8/2014 |
| JP | 2015-000093 A | 1/2015 |
| JP | 2016-052521 A | 4/2016 |
| JP | 2016-064155 A | 4/2016 |
| JP | 2016-073686 A | 5/2016 |
| JP | 2016-101506 A | 6/2016 |
| JP | 2017-176848 A | 10/2017 |
| WO | 2010/117685 A2 | 10/2010 |
| WO | 2014/146107 A1 | 9/2014 |

OTHER PUBLICATIONS

International Search Report dated Jul. 19, 2016 issued in PCT/JP2016/062567.

ENDOSCOPE APPARATUS

CROSS-REFERENCE TO RELATED APPLICATIONS

This is a continuation of International Application PCT/JP2016/062567 which is hereby incorporated by reference herein in its entirety.

This application is based on Japanese Patent Application No. 2015-098872, the contents of which are incorporated herein by reference.

TECHNICAL FIELD

The present invention relates to an endoscope apparatus.

BACKGROUND ART

In the related art, there is a known endoscope apparatus that has binocular lenses and with which an imaging subject can be three-dimensionally observed by acquiring two images thereof having parallax (for example, see Patent Literature 1).

CITATION LIST

Patent Literature

{PTL 1} Japanese Unexamined Patent Application, Publication No. 2007-151862

SUMMARY OF INVENTION

An aspect of the present invention is an endoscope apparatus including: an elongated insertion portion that is inserted into a body; an image-acquisition portion that has an imaging optical system disposed at a distal end of the insertion portion and that acquires two images having parallax for the same imaging subject; an identifying portion that identifies an image of an object, which is in close proximity to the imaging optical system, that is captured only in one of the two images acquired by the image-acquisition portion; and a close-proximity-image-removal processing portion that processes the image so that the image of the object identified by the identifying portion is removed from the image.

DESCRIPTION OF EMBODIMENT

An endoscope apparatus 1 according to an embodiment of the present invention will be described below with reference to the drawings.

Figure 1:
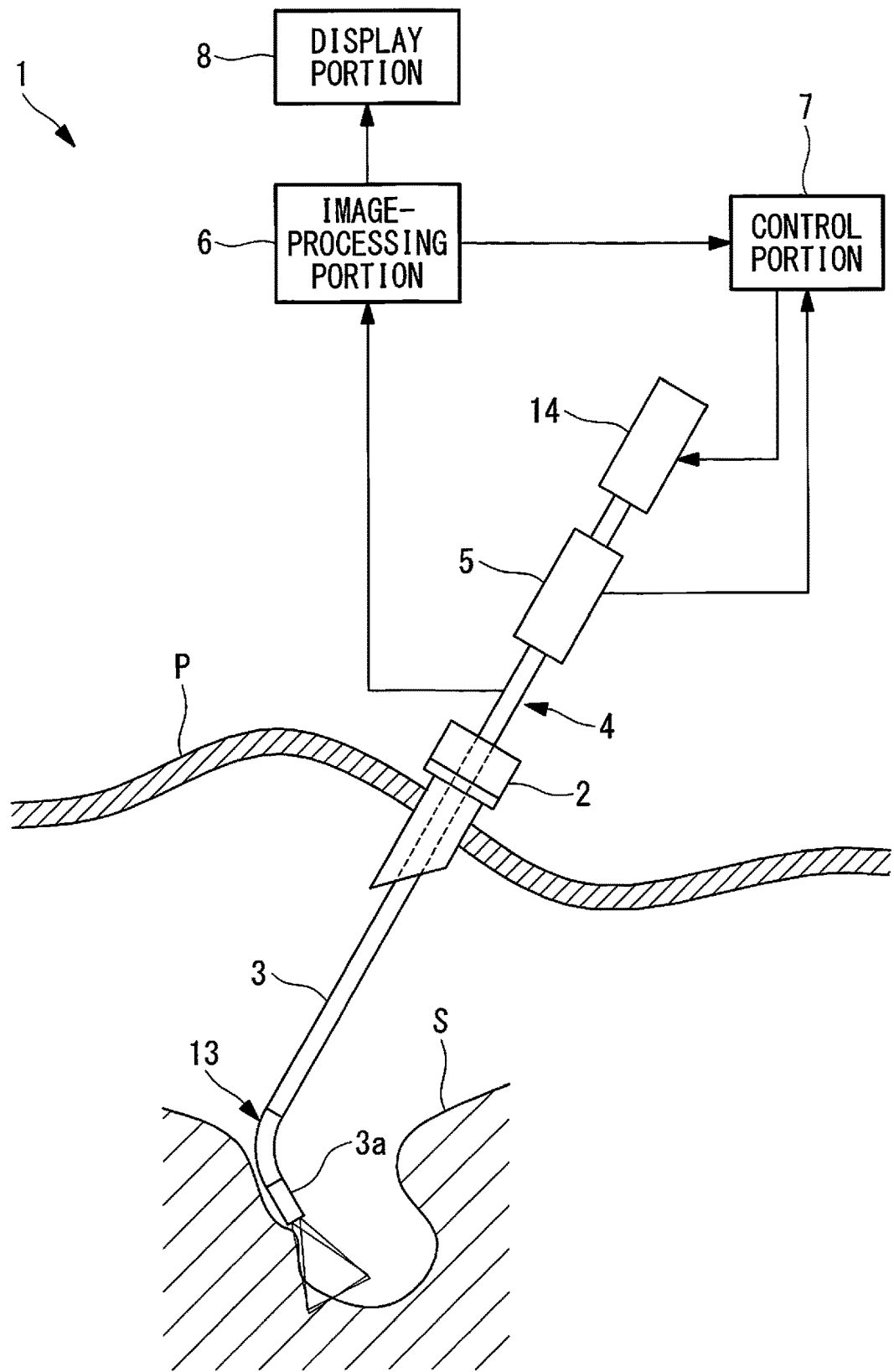
FIG. 1 is an overall configuration diagram showing an endoscope apparatus according to an embodiment of the present invention.

As shown in FIG. 1, the endoscope apparatus 1 according to this embodiment is provided with: an insertion portion 3 that is inserted into a body cavity by passing through an inner hole of a trocar 2 that is secured in a state in which the trocar 2 has passed through the skin P of a patient; an endoscope main unit 4 that acquires an image of the body cavity interior; a manipulating portion 5 for manipulating the endoscope main unit 4; an image-processing portion (identifying portion) 6 that processes the image acquired by the endoscope main unit 4; a control portion (close-proximity-image-removal processing portion) 7 that controls the endoscope main unit 4 on the basis of instruction signals input via the manipulating portion 5 and information acquired by the image-processing portion 6; and a display portion 8.

Figure 2:
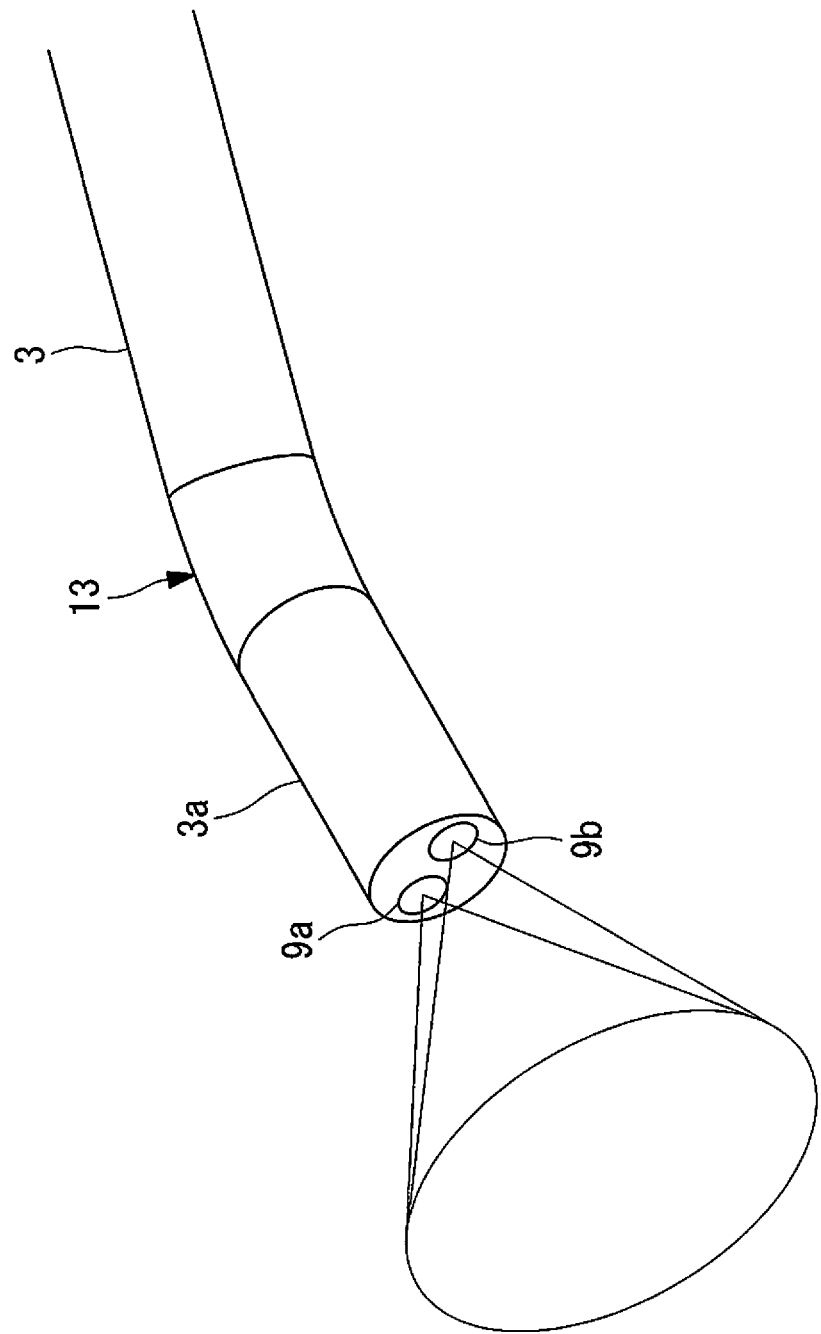
FIG. 2 is a perspective view showing a portion at a distal end of an insertion portion of the endoscope apparatus in FIG. 1.
Figure 3:
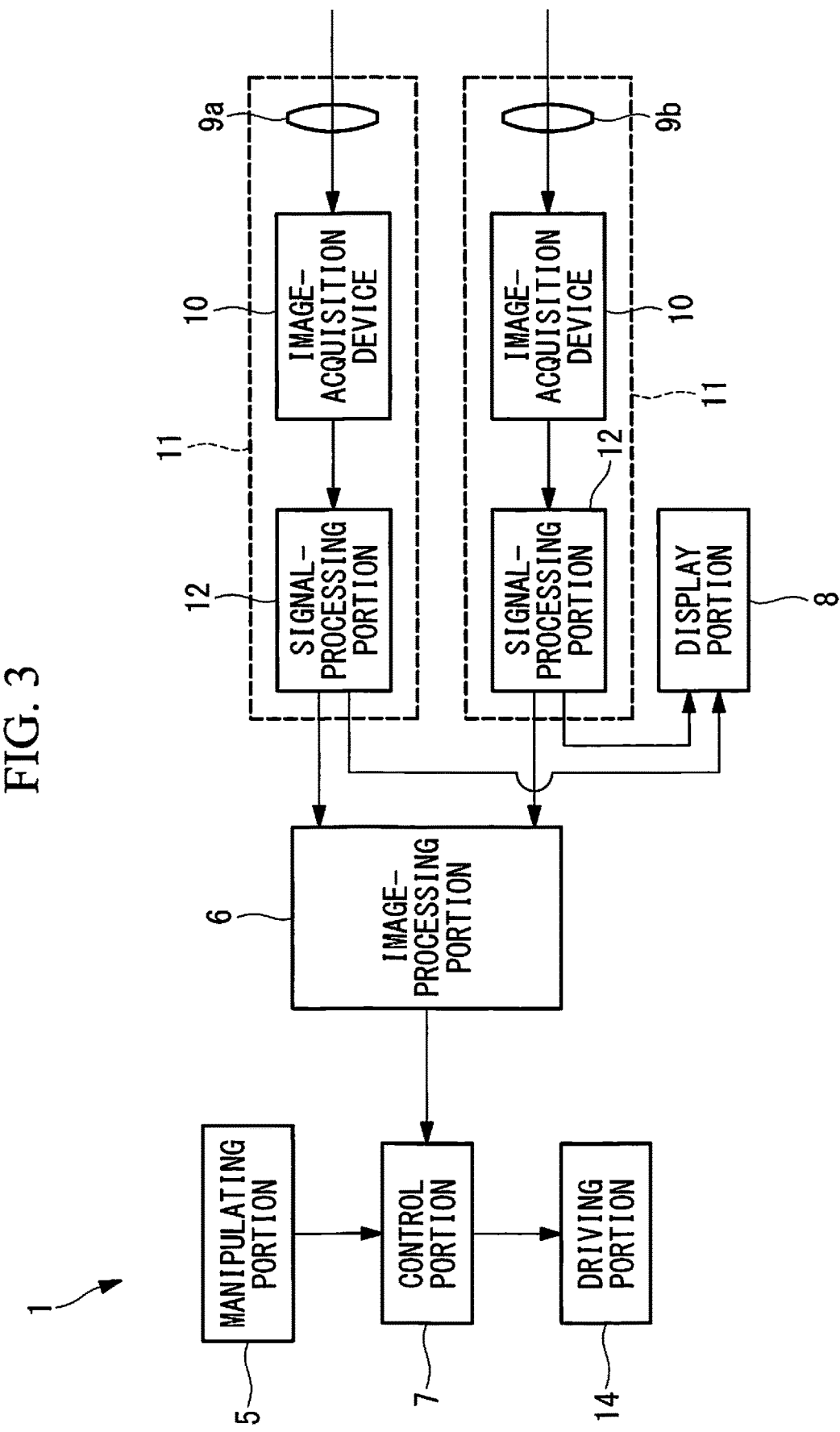
FIG. 3 is a block diagram showing the endoscope apparatus in FIG. 1.
Figure 5:
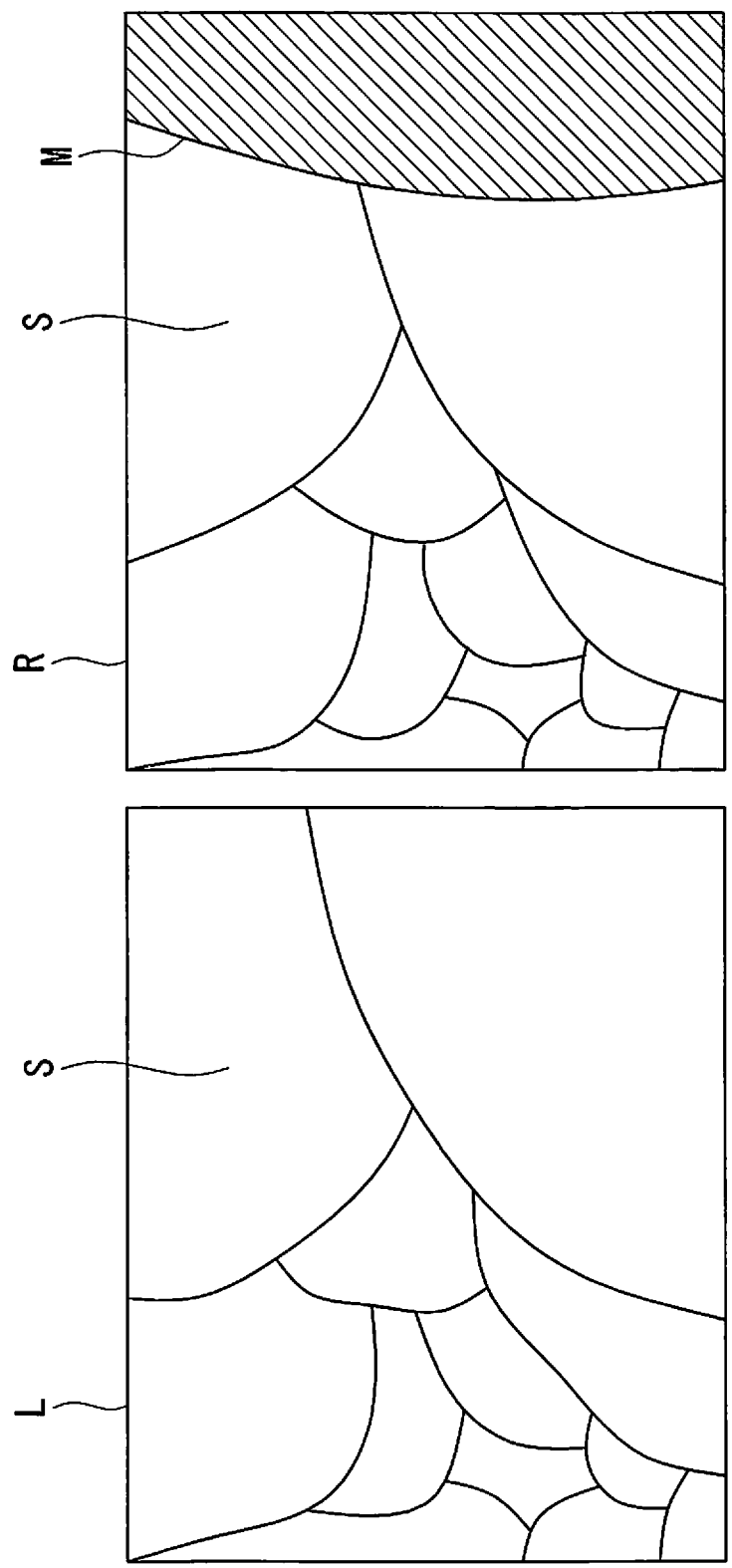
FIG. 5 is a diagram showing an example image that is acquired in the state shown in FIG. 4 and in which vignetting is occurring.

As shown in FIGS. 2 and 3, the endoscope main unit 4 is provided with image-acquisition portions 11 that are provided with: two objective lenses 9a and 9b that are disposed, at a distal-end surface of the elongated insertion portion 3, at positions that are separated in a radial direction of the insertion portion 3; and image-acquisition devices (imaging optical systems) 10 that capture light that comes from an imaging subject and that is collected by the individual objective lenses 9a and 9b. The optical axes of the two objective lenses 9a and 9b are arranged so as to intersect each other at a position that is farther forward than the distal end surface of the insertion portion 3. By doing so, as shown in FIG. 5, the image-acquisition devices 10 can acquire two images L and R having parallax for the same imaging subject.

In addition, as shown in FIG. 3, the image-acquisition portions 11 are provided with signal-processing portions 12 that generate image signals by processing the signals acquired by the image-acquisition devices 10. From the signal-processing portions 12, image signals that are in a displayable format are output to the display portion 8, and image signals that are in a format from which the color information has been removed and in which only the shape information is included are output to the image-processing portion 6.

In addition, as shown in FIGS. 2 and 3, the endoscope main unit 4 is provided with: a bending portion 13 that is capable of pivoting a distal-end portion 3a of the insertion portion 3, in which the image-acquisition portions 11 are provided, about an axis that is orthogonal to the longitudinal axis of the insertion portion 3; and a driving portion 14 that electrically moves the bending portion 13. When the bending portion 13 is actuated by the driving portion 14, the distal-end portion 3a is pivoted about an axis that is orthogonal to the longitudinal axis of the insertion portion 3. By doing so, the directions of the optical axes of the objective lenses 9a and 9b are changed, and thus, it is possible to change the viewing fields.

The image-processing portion 6 uses the image signals output from the signal-processing portions 12 to identify feature points in the two sets of image signals by means of a publically known method such as block matching or the like, thus identifying image regions that exist only in one of the images.

Figure 4:
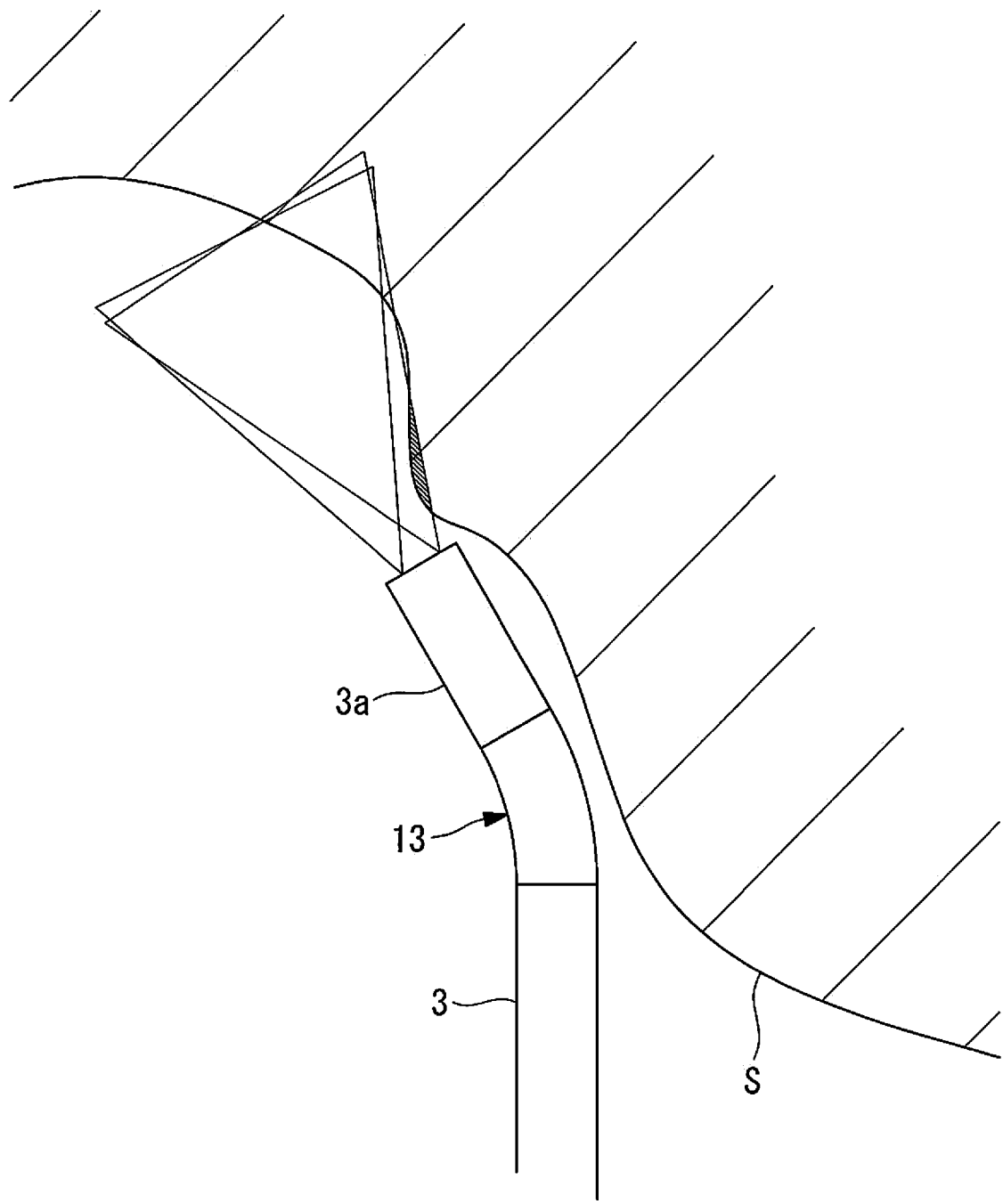
FIG. 4 is a diagram showing a state in which, in the endoscope apparatus in FIG. 1, peripheral tissue is in close proximity to the right objective lens on the right side thereof.

For example, in the case in which observation is performed by inserting the distal end of the insertion portion 3 into a relatively small space such as the pelvic cavity, as shown in FIG. 4, there are cases in which an inner wall S of the space is in close proximity to one of the objective lenses 9a and 9b on one side thereof. In the case shown in the figure, an inner wall (object) S of the space is in close proximity to the right objective lens 9a on the right side thereof. Thus, in this case, two images L and R shown in FIG. 5 are acquired.

With FIG. 5, in the right image R acquired via the right objective lens 9a, an image (close-proximity object image) M of the inner wall S of the space exists in a portion on the right side of the image R (the portion indicated by hatching in FIG. 5), which does not exist in the left image L acquired via the left objective lens 9b. The image-processing portion 6 compares the two sets of image signals to identify the close-proximity object image M in the right image R, and transmits information about this fact and information about the position at which the close-proximity object image M has been identified in the right image R to the control portion 7.

The manipulating portion 5 may be an arbitrary input portion such as a handle, a push button, a sliding switch, or the like. For example, in the case of a handle, instruction signals indicating the direction and the angle to which the bending portion 13 is pivoted can be input by means of the rotating angle and the rotating direction of the handle.

The driving portion 14 is provided with a motor (not shown) that causes the distal-end portion 3a of the insertion portion 3 to be pivoted in the arraying direction (left-to-right direction) of the right and left objective lenses 9a and 9b and a motor (not shown) that causes the distal-end portion 3a to be pivoted in a direction orthogonal to said direction (top-to-bottom direction), and one of or both of the motors are driven in accordance with the instruction signals.

The control portion 7 controls the driving portion 14 on the basis of the instruction signals input by manipulating the manipulating portion 5. In addition, the control portion 7 controls the driving portion 14 on the basis of the information transmitted thereto from the image-processing portion 6. Specifically, upon receiving the information indicating that the close-proximity object image M has been identified from the image-processing portion 6, on the basis of the information about the position at which the close-proximity object image M has been identified, which is simultaneously received from the image-processing portion 6, the driving portion 14 is controlled so that the distal-end portion 3a is pivoted in the direction opposite from said position.

Figure 6:
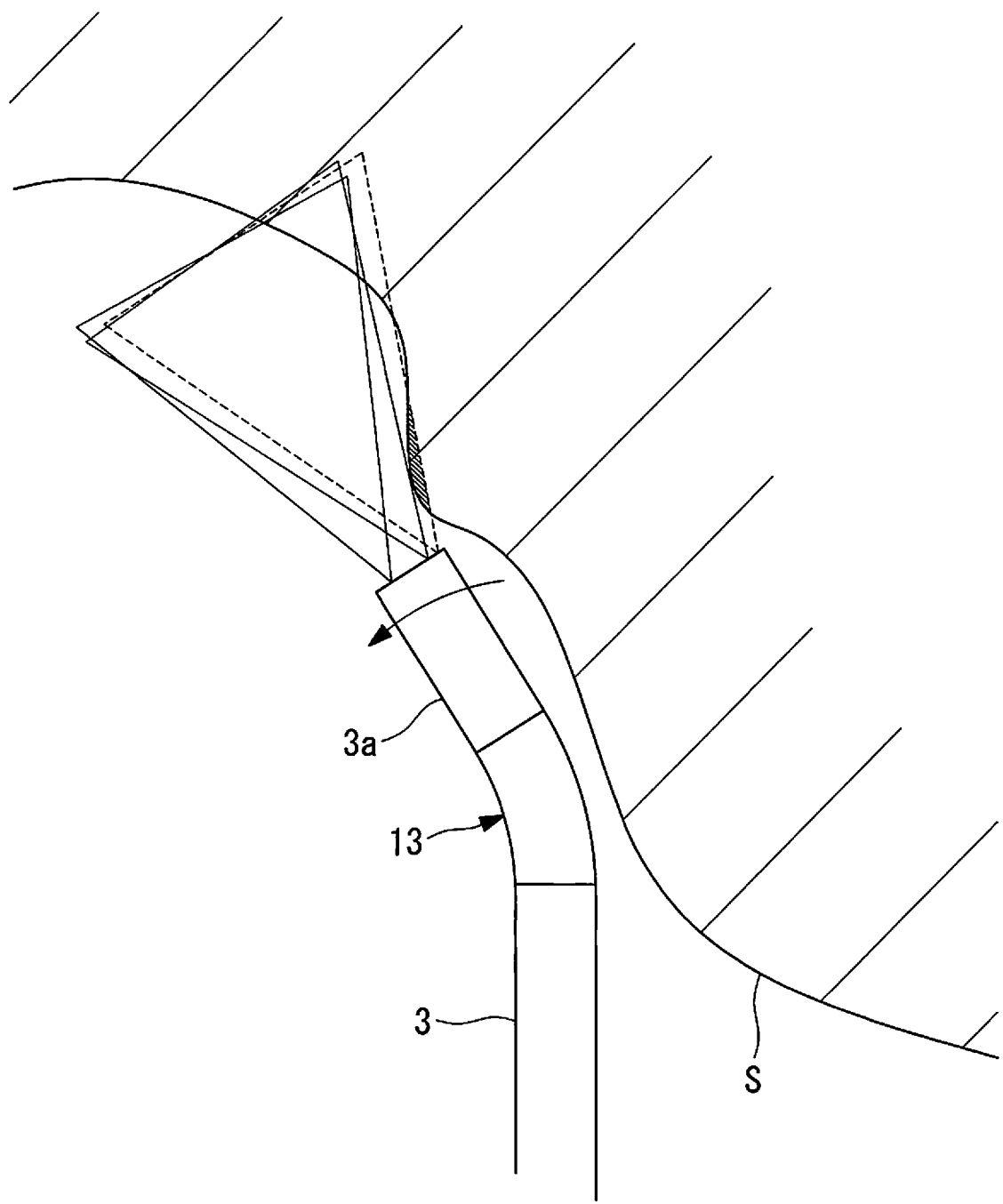
FIG. 6 is a diagram showing a state in which vignetting is eliminated by operating a bending portion from a state shown in FIG. 1.

More specifically, as has been described above, in the case in which the close-proximity object image M is identified in a region on the right side of the right image R, the control portion 7 controls the driving portion 14 so as to move the distal-end portion 3a leftward, as shown in FIG. 6, in other words, so that the distal-end portion 3a is pivoted by a predetermined angle in a direction opposite from the position in the image R at which the close-proximity object image M has been identified. The angle by which the distal-end portion 3a is pivoted by the driving portion 14 may be set to be an angle that is large enough to move the viewing fields so as to eliminate the close-proximity object image M from the right image R.

The operation of the thus-configured endoscope apparatus 1 according to this embodiment will be described below.

In order to observe the body interior of the patient by using the endoscope apparatus 1 according to this embodiment, the insertion portion 3 of the endoscope main unit 4 is inserted into the body from the distal-end portion 3a side via the trocar 2, and the image signals in the body interior are acquired by operating the image-acquisition portions 11.

An operator manipulates the manipulating portion 5 to input the instruction signals for moving the bending portion 13. When the instruction signals are input, the control portion 7 controls the driving portion 14 so as to bend the bending portion 13 by the angle and in the direction in accordance with the instruction signals input via the manipulating portion 5, thus moving the viewing fields of the image-acquisition portions 11 as instructed by the operator. Because the images L and R acquired by the image-acquisition portions 11 are transmitted to and displayed on the display portion 8, the operator can search for a site-to-be-observed in the body interior by using the images L and R displayed on the display portion 8.

In this case, the image signals of the two images L and R acquired by the image-acquisition portions 11 are transmitted to the image-processing portion 6 and are compared with each other, and thus, the close-proximity object image M that exists only in one of the images is identified. Then, when the close-proximity object image M is identified, the information about this fact and the position of the close-proximity object image M in the image L or R is transmitted to the control portion 7.

When the control portion 7 receives the information indicating that the close-proximity object image M has been identified, the control portion 7 controls the driving portion 14 so as to move the viewing fields in the direction opposite from the position of the close-proximity object image M in the image L or R, thus bending the bending portion 13 by the predetermined angle. By doing so, as shown in FIG. 6, it is possible to remove the close-proximity object image M from the viewing fields by moving the viewing fields in the direction opposite from the close-proximity object image M.

In other words, the brain of the operator who is performing observation by displaying, on the display portion 8, the images L and R having parallax acquired by the image-acquisition portions 11 performs, on the basis of the two images L and R, image fusion into a three-dimensional image, thus allowing the operator to concentrate on observing the state of the body interior by using the three-dimensional image, and therefore, the operator often does not notice the close-proximity object images M captured in the individual images L and R. Thus, in the case in which the operator performs observation for a long period of time without becoming aware of the occurrence of so-called vignetting, in which the close-proximity object image M is captured only in one of the images, visually-induced motion sickness due to binocular rivalry occurs, and thus, the efficiency at which the procedures are performed is deteriorated because the procedures are performed by using disorienting images.

With this embodiment, in the case in which vignetting occurs in the image L or R, because the close-proximity object image M is identified by the image-processing portion 6, and the control portion 7 controls the driving portion 14 so that the close-proximity object does not appear in the viewing fields, even in the case in which the operator is not aware of the occurrence of vignetting, the occurrence of visually-induced motion sickness due to binocular rivalry is decreased, and thus, there is an advantage in that the efficiency at which the procedures are performed is enhanced by preventing the procedures from being performed by using disorienting images.

Figure 7:
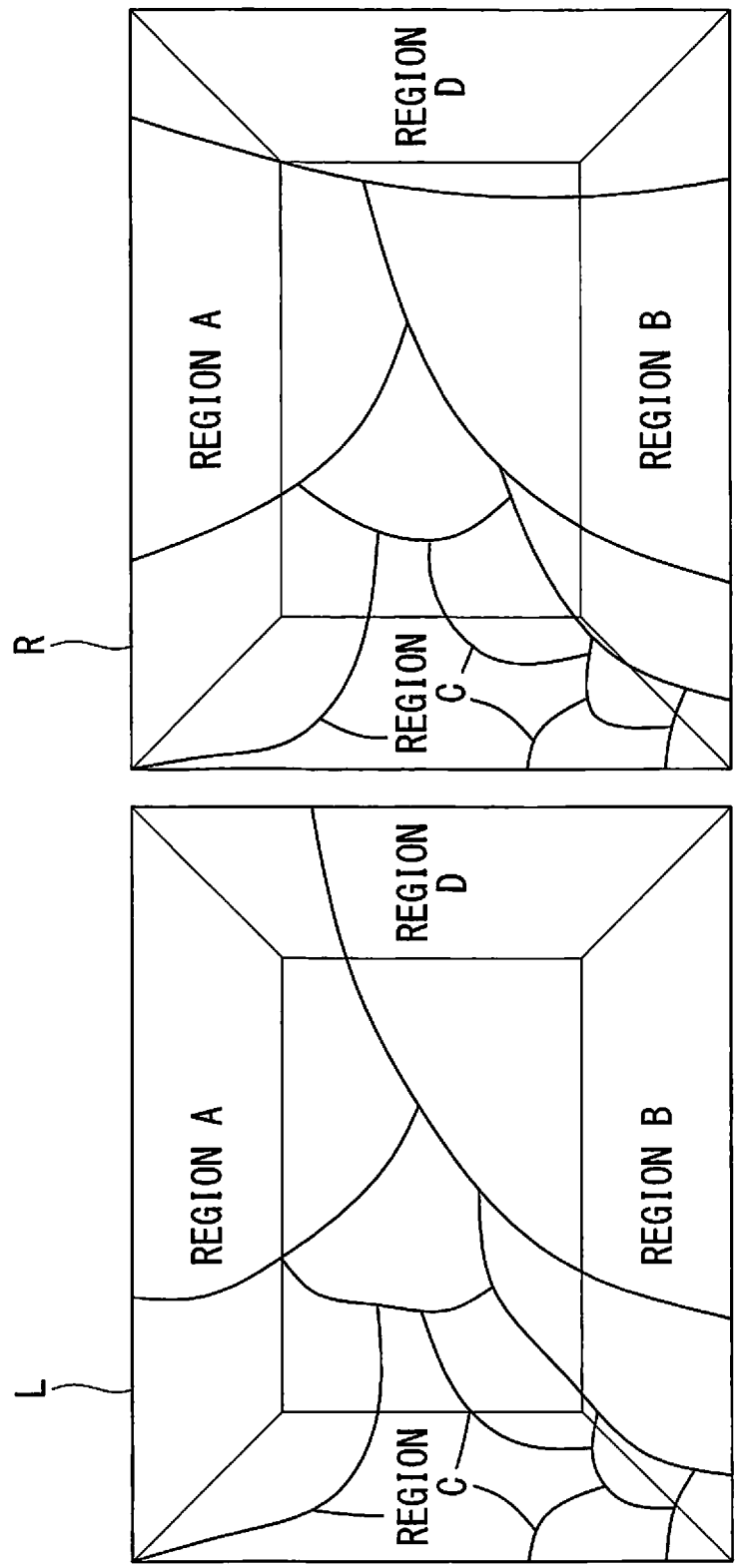
FIG. 7 is a diagram showing a modification of a region used to identify a close-proximity object image in the endoscope apparatus in FIG. 1.

Note that, in the endoscope apparatus 1 according to this embodiment, the entirety of the two images L and R may be compared in order to identify the close-proximity object image M that causes vignetting to occur. Alternatively, because vignetting in the image occurs in peripheral regions of the image L or R, as shown in FIG. 7, the presence/absence of the close-proximity object image M and the position thereof in the image L or R may be determined by comparing the two images L and R only with respect to peripheral regions (regions A to D) of the images L and R. By doing so, it is possible to take action by quickly detecting the presence/absence of vignetting and the position thereof because of the small amount of calculation.

Figure 8:
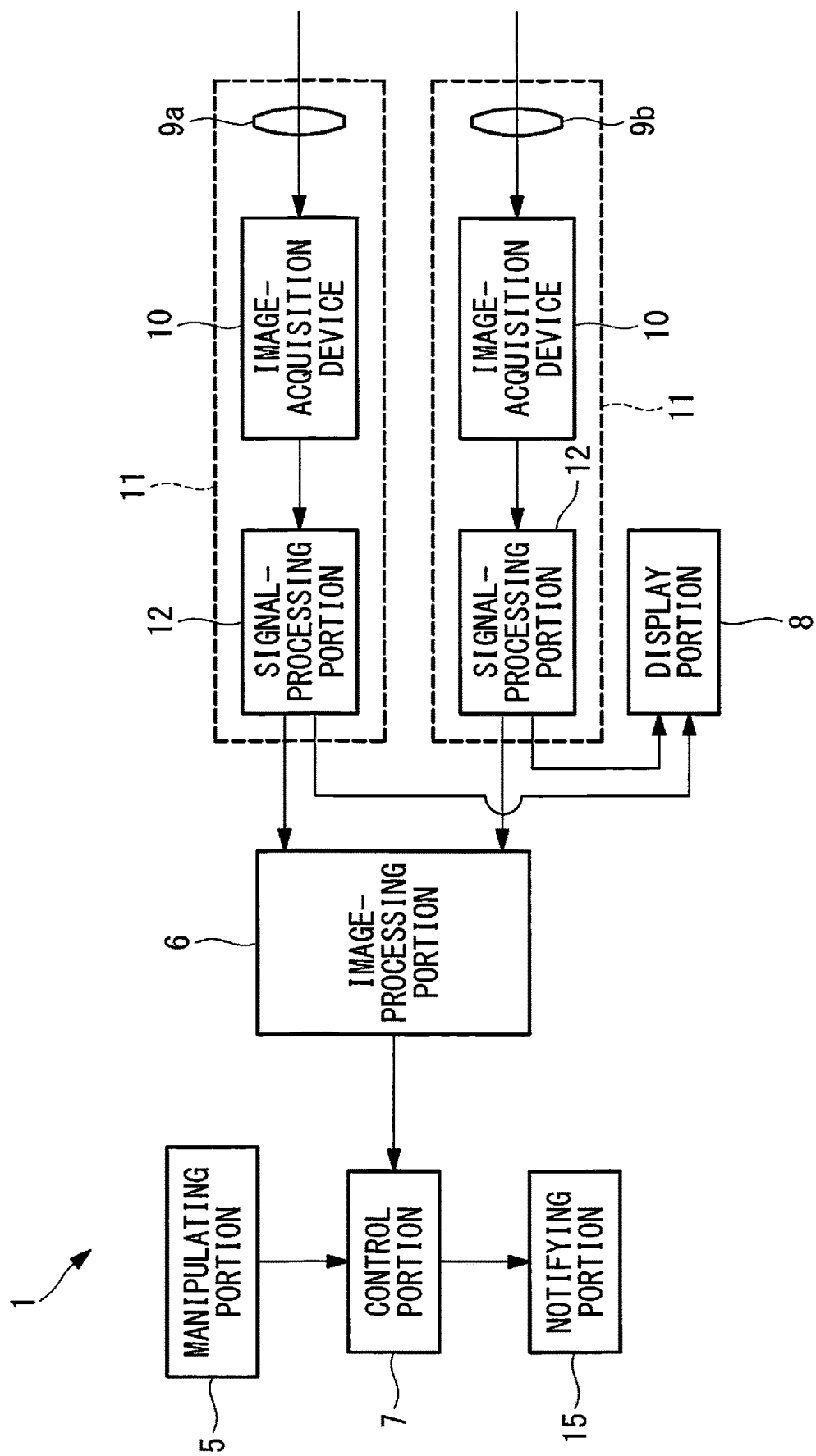
FIG. 8 is a block diagram showing a modification of the endoscope apparatus in FIG. 3.

In addition, in the case in which vignetting occurs in the image L or R, vignetting is eliminated by identifying the occurrence thereof and by shifting the viewing fields by actuating the bending portion 13; however, alternatively, a notifying portion (close-proximity-image-removal processing portion) 15 that, in the case in which vignetting occurs, simply notifies the occurrence thereof may be provided, as shown in FIG. 8.

In other words, vignetting causes the efficiency at which the procedures are performed to be deteriorated because observation is continued without being aware of the occurrence of vignetting. Therefore, by making the operator aware of the occurrence of vignetting by notifying him/her of this fact, it is possible to manually actuate the bending portion 13 by manipulating the manipulating portion 5 so that the close-proximity object does not appear in the viewing fields.

As the method of issuing a notification by means of the notifying portion 15, it is possible to employ a notifying method in which the operator viewing the images L and R is made aware of the occurrence of vignetting by changing the color or the like of the close-proximity object image M identified in the image L or R or a notifying method based on sound, vibrations, or the like.

In addition, when issuing a notification about the occurrence of vignetting, an arrow or the like may be displayed to indicate the direction to which the bending portion 13 is to be bent in order to eliminate vignetting or an audio instruction therefor may be given. By doing so, it is possible to prompt the operator to eliminate vignetting.

In addition, when vignetting occurs in the image L or R, the image-processing portion (close-proximity-image-removal processing portion) 6 may perform image processing so as to remove the close-proximity object image M identified by the image-processing portion 6. For example, as the method of removing the close-proximity object image M in the image L or R, it is conceivable to create a black-defect state by decreasing the luminance of the region including the identified close-proximity object image M or to create an overexposed state by increasing the luminance.

In addition, in this embodiment, although it is assumed that the two images L and R having parallax are acquired for the same imaging subject by using the image-acquisition portions 11 provided with the two objective lenses 9a and 9b that are disposed at the left and right with a spacing therebetween, alternatively, by using an optical optical-path changing means, such as a variable stop, a liquid crystal shutter, or the like, the two images L and R having parallax may be acquired for the same imaging subject by means of a single objective lens 9 and a single image-acquisition device 10. By doing so, it is possible to reduce the size of the distal-end portion 3a of the insertion portion 3.

Figure 9:
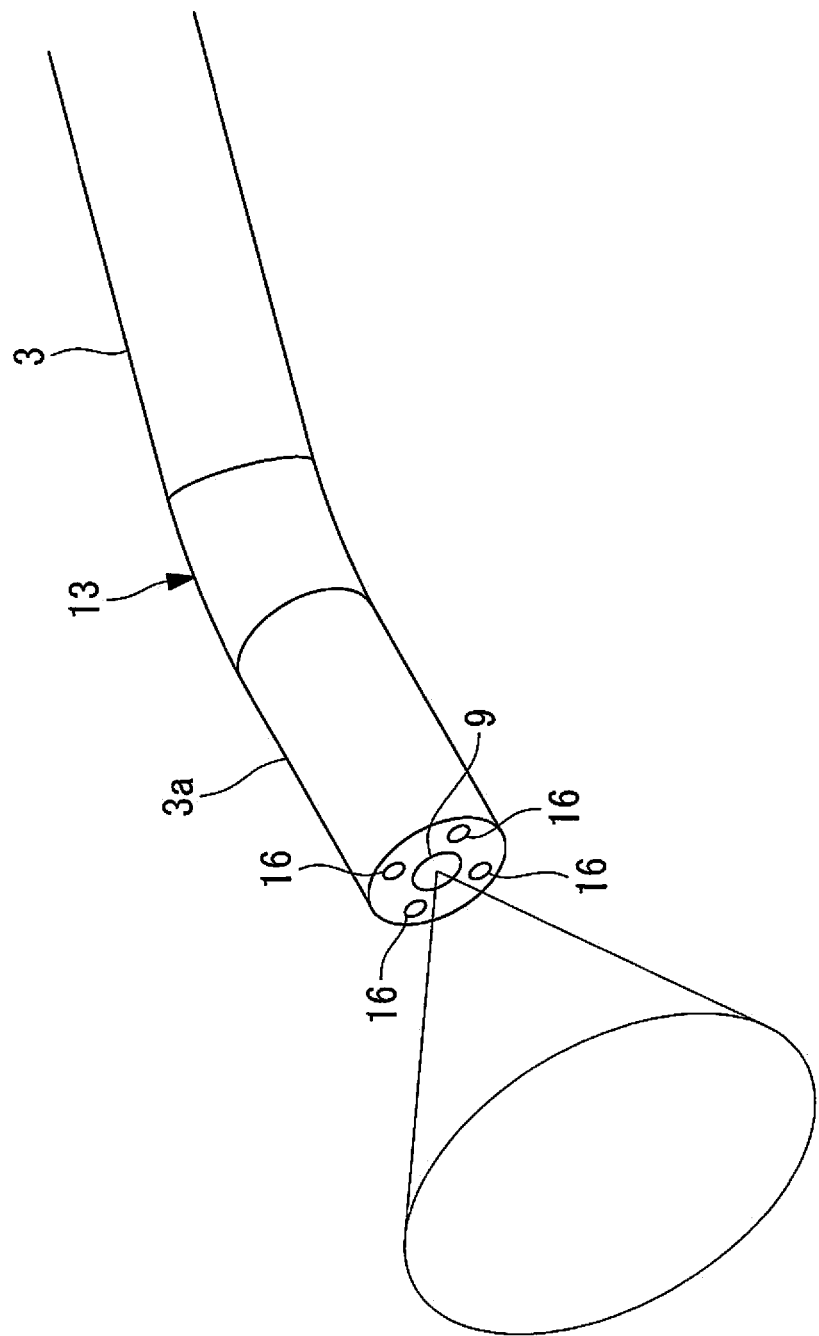
FIG. 9 is a perspective view showing a portion at a distal end of an insertion portion of another modification of the endoscope apparatus in FIG. 1.

In this case, as shown in FIG. 9, an auxiliary image-acquisition portion that includes auxiliary objective lenses 16 for detecting close-proximity objects may be provided in the area surrounding a main objective lens 9 for acquiring the images L and R having parallax. With the auxiliary image-acquisition portion that specially designed to detect close-proximity objects, it is possible to enhance the precision of identifying close-proximity objects.

In addition, in the case in which vignetting occurs in the image L or R, the operator may be allowed to switch between a mode in which the apparatus is operated so as to eliminate vignetting and a mode in which vignetting is not eliminated even if vignetting occurs.

The above-described embodiment leads to the following invention.

An aspect of the present invention is an endoscope apparatus including: an elongated insertion portion that is inserted into a body; an image-acquisition portion that has an imaging optical system disposed at a distal end of the insertion portion and that acquires two images having parallax for the same imaging subject; an identifying portion that identifies an image of an object, which is in close proximity to the imaging optical system, that is captured only in one of the two images acquired by the image-acquisition portion; and a close-proximity-image-removal processing portion that processes the image so that the image of the object identified by the identifying portion is removed from the image.

With this aspect, when the two images having parallax are acquired for the same imaging subject by using the image-acquisition portion via the imaging optical system disposed at the distal end of the insertion portion by inserting the distal end of the insertion portion into a small space in the body, in the case in which the image of the object in close proximity to the imaging optical system is captured in only one of the two acquired images, the identifying portion identifies the object image and the close-proximity-image-removal processing portion processes the image so as to remove the object image from the image. As a result, it is possible to prevent the occurrence of so-called vignetting in which an object in close proximity is captured only in one of the images. Therefore, the occurrence of visually-induced motion sickness due to binocular rivalry is decreased, and thus, it is possible to enhance the efficiency at which the procedures are performed by preventing the procedures from being performed by using disorienting images.

In the above-described aspect, the insertion portion may be provided with a bending portion that is bent so as to change an angle of an optical axis of the imaging optical system, and the close-proximity-image-removal processing portion may control the bending portion so that the object is placed outside the viewing field of the imaging optical system.

By doing so, in the case in which the identifying portion identifies an image of the object, which is in close proximity to the imaging optical system, that is captured only in one of the images, the close-proximity-image-removal processing portion controls the bending portion, thereby changing the angle of the optical axis of the imaging optical system, and the object is placed outside the viewing field of the imaging optical system. By doing so, it is possible to easily remove the image of the object in close proximity to the imaging optical system from the image. Because the image of the object is often captured in a peripheral portion of the image, it is possible to remove the image of the object from the image just by slightly changing the angle of the optical axis of the imaging optical system.

In addition, in the above-described aspect, the close-proximity-image-removal processing portion may issue a notification indicating that the image of the object has been identified by the identifying portion.

By separately viewing, with both of the left and right eyes, the two images having parallax acquired by the image-acquisition portion, the brain performs three-dimensional image fusion of the two images. Because the operator who is concentrating on performing the procedures while observing the state of the body interior by using the three-dimensional image is ascertaining the state of the body interior by using the image generated by means of image fusion, it is difficult for the operator to become aware of the occurrence of vignetting, even when vignetting occurs in the image and the operator is experiencing a sense of dissonance; and thus, visually-induced motion sickness due to binocular rivalry tends to occur when the procedures take a long period of time. With this aspect, by issuing a notification about vignetting when it occurs in the image, the operator is made aware of the occurrence of vignetting, and thus, it is possible to prompt the operator to perform the operation for removing the image of the object from the image.

In addition, in the above-described aspect, the close-proximity-image-removal processing portion may give an instruction about a direction in which the imaging optical system is moved in order to place the object outside the viewing field of the imaging optical system.

By doing so, because the close-proximity-image-removal processing portion gives instructions for moving the imaging optical system in an appropriate direction when vignetting occurs in the image, the operator who has become aware of vignetting can quickly remove the image of the object from the image, and thus, it is possible to eliminate vignetting in an early stage.

In addition, in the above-described aspect, the close-proximity-image-removal processing portion may process the image so as to remove the image of the object captured in the image.

By doing so, it is possible to eliminate vignetting in an early stage by processing the image, and thus, it is possible to enhance the efficiency at which the procedures are performed by preventing the procedures from being performed by using disorienting images.

REFERENCE SIGNS LIST 1 endoscope apparatus
3 insertion portion
6 image-processing portion (identifying portion, close-proximity-image-removal processing portion)
7 control portion (close-proximity-image-removal processing portion)
10 image-acquisition device (imaging optical system)
11 image-acquisition portion
13 bending portion
15 notifying portion (close-proximity-image-removal processing portion)
L, R image

The invention claimed is:

1. An endoscope apparatus comprising:
an elongated insertion portion configured to be inserted into a body;
an image-acquisition portion that has an imaging optical system disposed at a distal end of the insertion portion and that acquires two images having parallax for the same imaging subject;
a bending portion that is provided in the insertion portion, the bending portion being bent so as to change an angle of an optical axis of the imaging optical system; and
a processor comprising hardware, the processor being configured to:
identify an image of an object, which is in close proximity to the imaging optical system, that is captured only in one of the two images acquired by the image-acquisition portion; and
bend the bending portion so that the image of the identified object is outside of the viewing field of the one of the two images.

2. An operation method of an endoscope apparatus which includes an image-acquisition portion having an imaging optical system disposed at a distal end of an elongated insertion portion that is inserted into a body, the method comprising:
acquiring two images having parallax for the same imaging subject by the image-acquisition portion;
identifying an image of an object, which is in close proximity to the imaging optical system, that is captured only in one of the two images acquired by the image-acquisition portion; and
bending a bending portion provided in the insertion portion, the bending portion being bent so as to change an angle of an optical axis of the imaging optical system, so that the identified image of the object is outside the viewing field of the one of the two images.

* * * * *